(12) United States Patent
Beden et al.

(10) Patent No.: US 7,648,627 B2
(45) Date of Patent: Jan. 19, 2010

(54) DEVICE FOR TREATING A MEDICAL LIQUID

(75) Inventors: Josef Beden, Mainz-Kastel (DE); Uwe Hahmann, Durmersheim (DE); Martin Herklotz, Heusenstamm (DE); Martin Lauer, St. Wendel (DE); Joachim Manke, Loehnberg (DE); Peter Scheunert, Friedrichsdorf (DE); Manfred Weis, St. Wendel (DE); Alexander Bongers, Langen (DE)

(73) Assignee: Fresenius Medical Care Deutschland GmbH, Bad Hamburg (DE)

( * ) Notice: Subject to any disclaimer, the term of this patent is extended or adjusted under 35 U.S.C. 154(b) by 283 days.

(21) Appl. No.: 10/516,528

(22) PCT Filed: May 22, 2003

(86) PCT No.: PCT/EP03/05377

§ 371 (c)(1),
(2), (4) Date: Dec. 2, 2004

(87) PCT Pub. No.: WO03/101510

PCT Pub. Date: Dec. 11, 2003

(65) Prior Publication Data
US 2005/0230292 A1    Oct. 20, 2005

(30) Foreign Application Priority Data
Jun. 4, 2002    (DE) ................. 102 24 750

(51) Int. Cl.
*A61M 1/10* (2006.01)
*B01D 65/00* (2006.01)
(52) U.S. Cl. ............... 210/85; 210/321.6; 604/6.01
(58) Field of Classification Search ............... 210/85, 210/321.6; 604/6.01
See application file for complete search history.

(56) References Cited

U.S. PATENT DOCUMENTS

| 4,436,620 | A | | 3/1984 | Bellotti et al. | |
|---|---|---|---|---|---|
| 4,479,762 | A | * | 10/1984 | Bilstad et al. | 417/395 |
| 4,927,411 | A | | 5/1990 | Pastrone et al. | |
| 5,431,627 | A | | 7/1995 | Pastrone et al. | |
| 5,474,683 | A | * | 12/1995 | Bryant et al. | 210/646 |
| 5,628,908 | A | * | 5/1997 | Kamen et al. | 210/646 |
| 6,471,855 | B1 | * | 10/2002 | Odak et al. | 210/143 |
| 6,542,761 | B1 | | 4/2003 | Jahn et al. | |
| 6,645,166 | B2 | | 11/2003 | Scheunert et al. | |
| 6,695,803 | B1 | * | 2/2004 | Robinson et al. | 604/4.01 |
| 7,147,613 | B2 | * | 12/2006 | Burbank et al. | 604/5.01 |
| 7,195,607 | B2 | * | 3/2007 | Westberg et al. | 604/6.11 |
| 2002/0062109 | A1 | | 5/2002 | Lauer | |
| 2003/0042181 | A1 | | 3/2003 | Metzner | |
| 2003/0100882 | A1 | | 5/2003 | Beden et al. | |
| 2003/0220607 | A1 | * | 11/2003 | Busby et al. | 604/29 |
| 2004/0084647 | A1 | | 5/2004 | Beden et al. | |

(Continued)

FOREIGN PATENT DOCUMENTS

DE    198 37 667 A1    3/2000

(Continued)

*Primary Examiner*—Terry K Cecil
(74) *Attorney, Agent, or Firm*—Fish & Richardson P.C.

(57) ABSTRACT

An apparatus for the treatment of a medical liquid has a liquid treatment machine and a cassette that is insertable in the machine. The cassette has a rigid base body with fitted chambers and passages and a foil that covers the chambers and passages. Actuators and sensors are arranged in the liquid treatment machine for the operation of the apparatus with the inserted cassette such that cassettes are insertable in different integration shapes.

40 Claims, 11 Drawing Sheets

FOREIGN PATENT DOCUMENTS

| | | |
|---|---|---|
| DE | 100 42 324 C1 | 2/2002 |
| DE | 100 46 651 A1 | 4/2002 |
| DE | 100 53 441 A1 | 5/2002 |
| DE | 101 57 924 C1 | 5/2002 |
| DE | 101 43 137 C1 | 4/2003 |
| WO | WO 84/02473 | 7/1984 |
| WO | WO 98/22165 | 5/1998 |
| WO | WO 00/23140 | 4/2000 |
| WO | WO 00/33898 | 6/2000 |
| WO | WO 01/17605 A1 | 3/2001 |

* cited by examiner

DEVICE FOR TREATING A MEDICAL LIQUID

This is a nationalization of PCT/EP03/05377 filed May 22, 2003 and published in German.

BACKGROUND OF THE INVENTION

1. Field of Invention

The invention relates to an apparatus for the treatment of a medical fluid comprising a fluid treatment machine and a cassette insertable therein substantially consisting of a rigid base body of the cassette with fitted chambers and passages and a foil covering them.

2. Description of the Prior Art

Corresponding cassettes are used in medical engineering, in particular to convey dialysis fluid, blood and the like. Cassettes of this type are described e.g. in DE 198 37 667, WO 84/02473, WO 98/22165 or WO 00/33898.

A cassette is, for example, thus known from DE 198 37 667 A1 which consists of a base body of a cassette with fitted chambers and passages and which is closed by a flexible foil to cover the passages and chambers. It is already described there that the cassette is inserted into a special receiving chamber, e.g. in a dialysis machine. This chamber can, for example, be opened via a pivotable door. The cassette can be inserted into the chamber, with the flexible foil lying opposite a corresponding mating piece at the machine so that the cassette can be operated with the aid of actuators and sensors on the machine side.

Although such apparatus with cassettes have generally been described, the conventional extracorporeal blood circuits or blood tubing systems are usually present in a differential construction. This means that a functional division onto different components is present. Such components, for example bubble traps, flow chambers or injection positions, are connected to one another by tubes and are as a rule connected individually to the respective dialysis machine. The design of such blood tubing systems is very complex in manufacture and handling, with the corresponding effort naturally being extremely time consuming with more complex systems such as an online hemodiafiltration.

On the other hand, conventional extracorporeal blood circuits which are installed in this differential construction have the advantage that they can be designed substantially more flexibly for the respective treatment depending on the demand. The previously known apparatus for the use of cassettes namely had the problem associated with it that they are only usable for a very specific application.

SUMMARY OF THE INVENTION

It is therefore the object of the present invention to further develop a generic apparatus comprising a fluid treatment machine and a cassette insertable therein such that a large flexibility for different applications is made possible while maintaining the fast and simple exchangeability.

This object is solved in accordance with the invention by means of an apparatus that has the features of the fluid treatment machine and cassette as described herein. Actuators and sensors are arranged here in a generic apparatus for the treatment of a medical fluid for the operation of the apparatus with an inserted cassette such that cassettes are insertable in different integration shapes.

Due to the clearly defined arrangement of corresponding sensors and actuators, cassettes of different complexity can be inserted into the fluid treatment machine in accordance with the desired application. It is therefore not necessary here to provide different apparatus for different applications.

A cassette for a simple, standard hemodialysis can thus be insertable here, for example. The corresponding pump chambers, measuring sensors and further actuators such as valves, etc. are here provided at pre-determined locations in the fluid treatment machine. Additional pumps, actuators, valves, etc. are provided in the fluid treatment machine which do not have to be actuated when the cassette is used for standard hemodialysis. They are, for example, only in use when a cassette is used for online hemodiafiltration or online hemofiltration, i.e. further passages, pump chambers, etc. are provided at corresponding positions in the corresponding cassettes which are associated with these actuators, pumps or valves. Furthermore, a cassette for an acute dialysis treatment can be inserted in which in turn the pumps, actuators and valves provided on the side of the fluid treatment machine are associated with corresponding pumping chambers, passages, etc. The associated control electronics can be selected depending on the inserted cassette for the control of the pumps, actuators, sensors, etc.

Particularly advantageous aspects of the invention result from the various embodiments of the apparatus described herein.

Cassettes in accordance with the invention for insertion into the aforesaid inventive apparatus are achieved with the various embodiments thereof that are described herein.

BRIEF DESCRIPTION OF THE DRAWINGS

Details and advantages of the invention will be explained in more detail by way of example in the following with reference to the Figures enclosed in the Annex. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
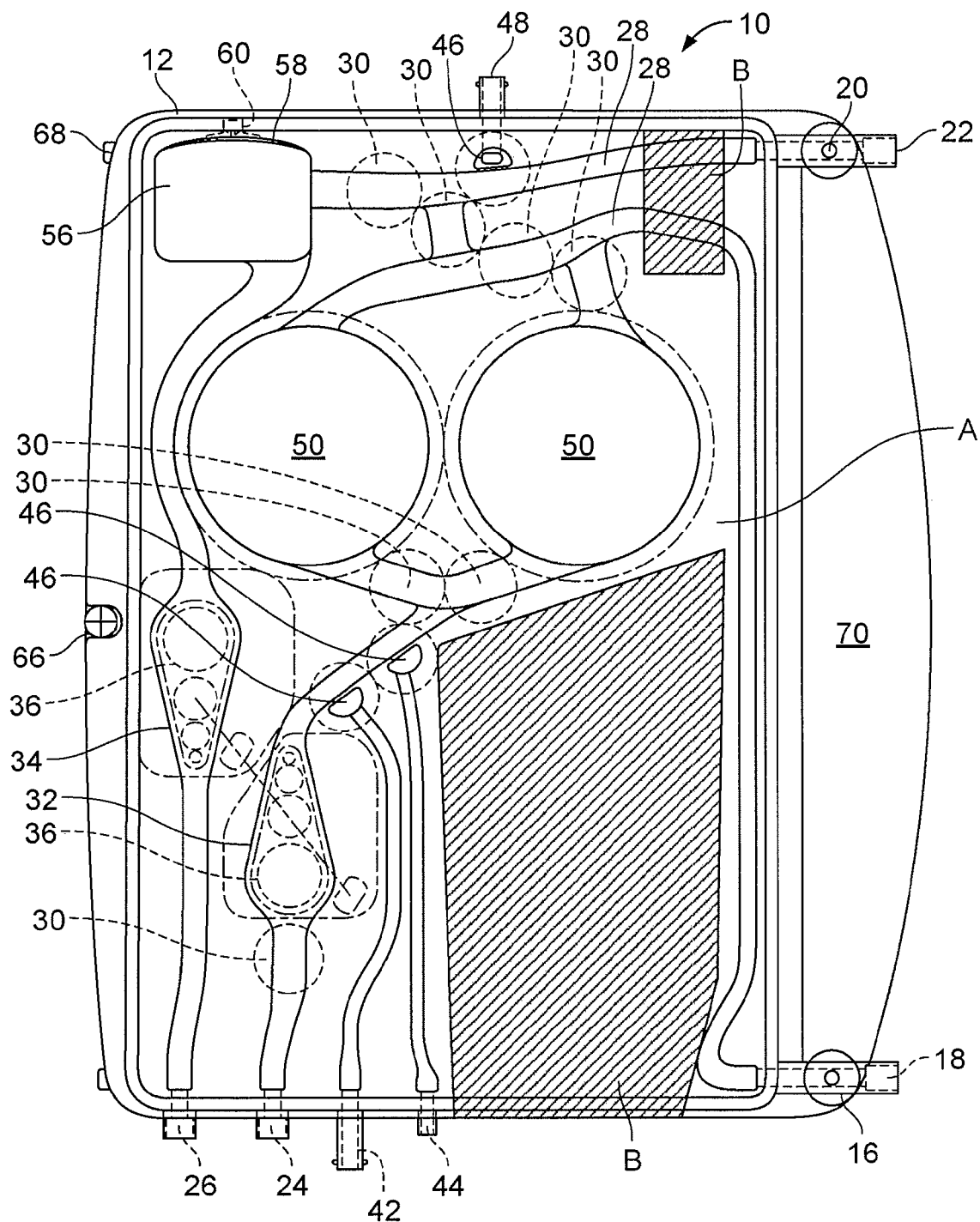
FIG. 1: a schematic plan view of a cassette for standard hemodialysis.

In FIG. 1, a cassette 10 in accordance with an embodiment variant of the present invention is shown which can be used in this embodiment for standard hemodialysis. In FIG. 1, the surface of the cassette 10 is divided into a hatched region B (two partial areas) and a non-hatched region A. Both the surface of the cassette 10 and the surface of the associated machine block (cf. FIG. 7) are divided into the covering surface regions A and B, with components of actuators or sensors to be coupled, which are common to all cassettes as basic variants, for example all the cassettes shown here for standard hemodialysis being accommodated in the surface region A (not hatched in FIG. 1) and with the surfaces B denoting regions in which actuators or sensors to be used optionally are provided in the machine block (cf. FIG. 7) and are only used as required, for example in cassettes in accordance with FIG. 2.

The cassette consists of a base body 12 of a cassette which consists of polypropylene in the embodiment shown here. A cover foil not shown in more detail here and consisting, for example, of a polyolefin elastomer mixture, is applied to the base body of the cassette. The passages and recesses, which will be looked at in more detail later, are covered by this cover foil 14. An arterial injection septum 16 is provided in the arterial line 18 to the dialyzer and a venous injection septum 20 is provided in the venous line 22 to the dialyzer. The dialyzer itself and the corresponding tube connection are not shown in any more detail in the embodiment shown here. Reference number 24 designates the blood inlet from the patient and 26 the blood outlet to the patient. The respective tubes, which likewise consist of a polyolefin elastomer mixture, are also not shown here for reasons of simplification. Passages 28 are recessed in the base body 12 of the cassette. They are acted on by a row of valves 30.

The design of these valves results, for example, from the German patent application DE 100 46 651 of the applicant to which reference is made in this respect. These valves 30 substantially have a valve body with a pressure passage and a sealing cap which cooperates with the valve body such that it closes the end of the pressure passage on the valve body side with respect to the environment, with a pressure space being able to be built up between the pressure passage and the sealing cap so that the sealing cap has a deformable sealing region for entry into the fluid passage in order to close this as required.

An arterial port 42 and a heparin port 44 is provided at the cassette which are each connected via corresponding passages to the passage carrying the arterial blood in each case via phantom valves 46. The phantom valves 46 are used in the cassette 10 in accordance with the invention instead of conventional open T-branches. In these phantom valves, the passage wall is not interrupted from the aspect of the main blood flow. The detailed design of these phantom valves results from the German patent application DE 100 53 441 of the same applicant to which reference is made here. Reference number 48 designates a venous port which likewise opens into a blood-carrying passage 28, here in the venous part of the blood-carrying passages, via a phantom valve 46.

An arterial port 42 and a heparin port 44 is provided at the cassette which are each connected via corresponding passages to the passage carrying the arterial blood in each case via phantom valves 46. The phantom valves 46 are used in the cassette 10 in accordance with the invention instead of conventional open T-branches. In these phantom valves, the passage wall is not interrupted from the aspect of the main blood flow. The detailed design of these phantom valves results from the German patent application DE 100 53 441 of the same applicant to which reference is made here. 48 designates a venous port which likewise opens into a blood-carrying passage 28, here in the venous part of the blood-carrying passages, via a phantom valve 46.

Figure 12:
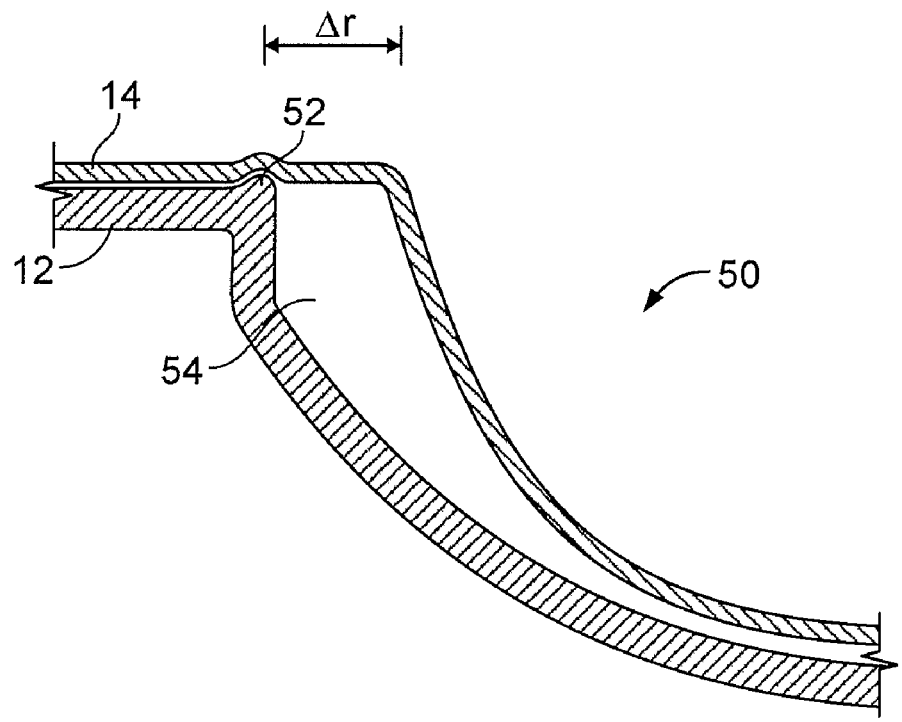
FIG. 12: a partially sectional representation of a pump chamber of the cassette in accordance with the present invention.

Reference number 50 designates two pump chambers which serve the pumping of the blood. The design of the pump chambers 50 results in detail from FIG. 12. The pump chambers 50 activated via membrane pumps provided at the machine side have substantially tangential inlets and outlets for a uniform throughflow of the total chamber, as already results from FIG. 1. The shape of the pump chambers 50 is pre-determined by the correspondingly shaped base body 12 of the cassette and can be approximately described as a spherical section. At the periphery, the base body of the cassette has a raised edge 52 around the pumping chambers 50 which serves as a stop bead. In addition, as results from FIG. 12, the peripheral edge of the spherical section is set somewhat lower so that in the pressing-out phase, that is in the phase in which the cover foil 14 is moved toward the base body 12 of the cassette, a flushing edge or flushing passage 54 is formed. The flushing edge or flushing passage 54 is advantageously made in that the spherical pump surface at the machine side which is not shown in FIG. 12 has a smaller radius than the radius of the pump chamber at the cassette side. The radius difference Δr is drawn in FIG. 12. A wide flushing edge or flushing passage 54 is hereby formed. This flushing edge or flushing passage 54 is an annular space for the pumped blood in the extreme pressing-out position. This free annular space, on the one hand, avoids blood damage by being trapped between the foil surface and the injection molded surface at the end of the pressing-out phase and, on the other hand, blood damage due to high flow speeds and shearing strains which would result at the start of the start-up phase if no free annular space were provided.

Figure 10:
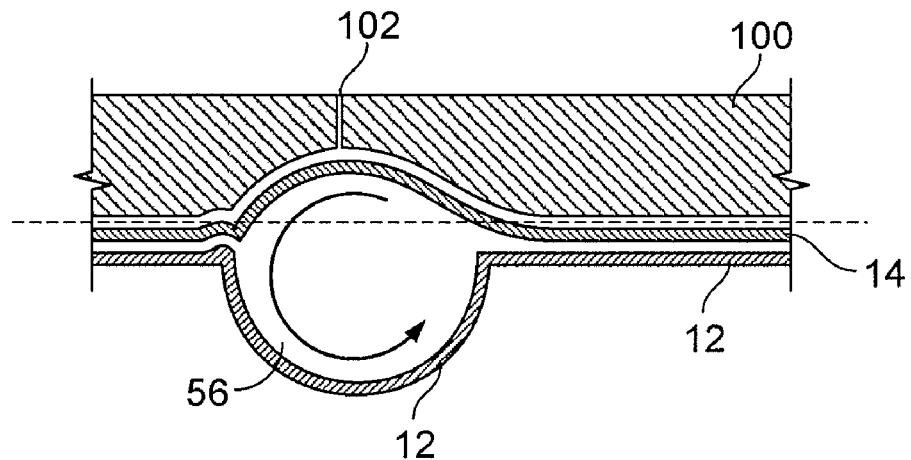
FIG. 10: a detail of a venting unit in the apparatus in accordance with the invention.
Figure 11:
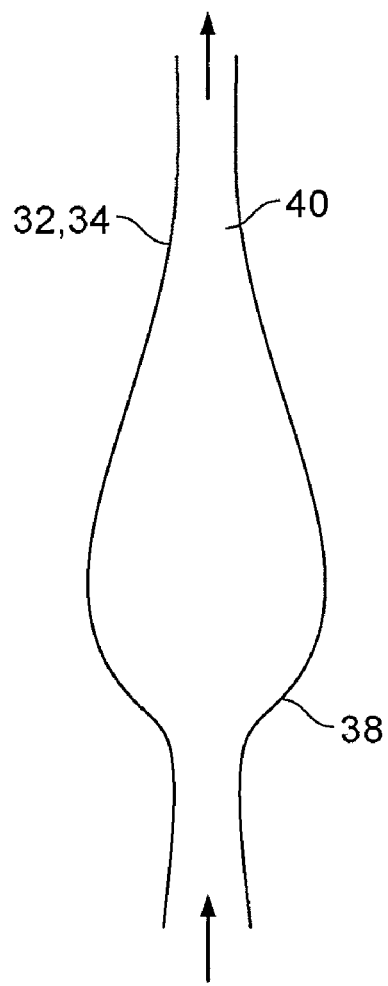
FIG. 11: a detailed view of a contour of a measuring chamber in a cassette in accordance with one of the aforesaid embodiment variants.

In the upper region of the cassette in the installed state, a venting chamber 56 is formed which is shown again in FIG. 10 in a sectional representation. A venting membrane 58 is arranged in this venting chamber via which correspondingly collected air can be separated since it is made as a partially permeable membrane which preferably has hydrophobic or oleophobic properties. Expanded or sintered polytetrafluoroethylene can preferably be used as the venting membrane. A venting stub 60 is arranged above the venting membrane 58 and its cooperation with the fluid treatment machine (not shown in more detail here) will be described later.

Bubbles are trapped in the venting chamber 56 by a slowing down of the blood flow. As shown in FIG. 10, a rotation flow is generated for effective air separation with minimum area requirements on the cassette 10. In this process, the generation of the final rotation flow is only created in the operating state of the cassette 10 in the fluid treatment machine 100 (cf. FIG. 10). The cover foil 14 of the cassette 10 is pulled into the fluid treatment machine by a corresponding vacuum coupling system of which only one vacuum suction passage 102 is shown in FIG. 10. An almost circular cross-section of the venting chamber 56 is thereby formed. The rotation flow of the blood is supported in that the passage opening into the venting chamber 56 also runs—together with its cover foil 14—slightly into the machine side so that an almost tangential inflow within the chamber is achieved. An effective suction can take place at the machine side at the venting stub 60. A low filling volume results overall here in the venting chamber 56 as a result of the construction.

Figure 13:
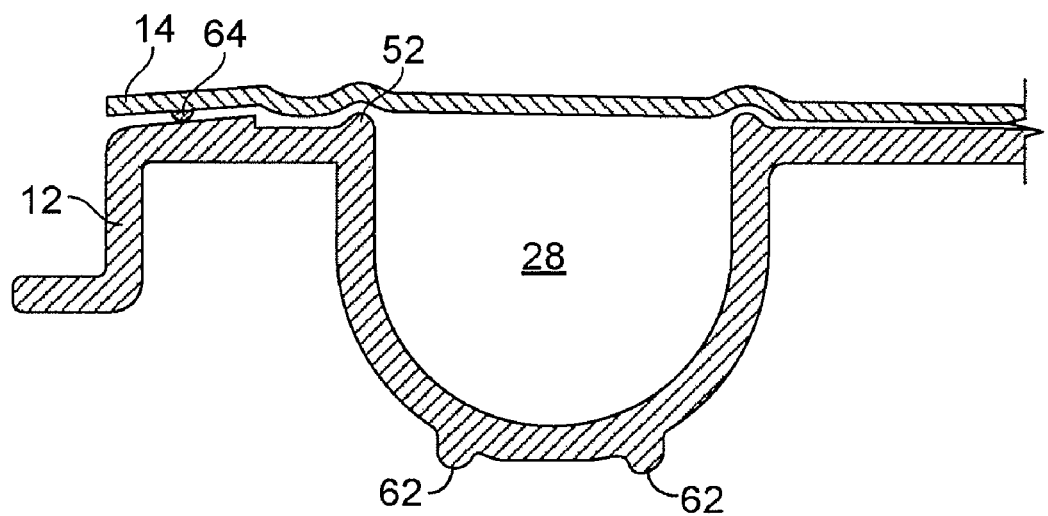
FIG. 13: a partially sectional representation through a passage of the cassette in accordance with an embodiment variant of the invention.

The basic design of the passages 28 can be explained with reference to FIG. 13. Generally, care is taken in the passage design of the passages 28 that a smooth foil surface and smooth passage surfaces are provided. Steps, dead spaces, turbulence and impact surfaces are avoided. Low changes in direction and speed are aimed for. Separations of flow are largely avoided. All passages 28 and also chambers 50 have an edge bead 52 (cf. also FIG. 12) which accompanies the passages and faces the cover foil 14. On insertion of the cassette 10 into the fluid treatment machine 100, the foil 14 is pressed onto the edge bead 52 such that all passages 28 are sealed against the environment. At the rear of the cassette, i.e. at the outer side of the passage wall, webs 62 are formed which accompany the passages and via which the rear pressing force is guided to the edge beads 52 in order thus to achieve a uniform linear distribution of force.

It can also be explained with reference to FIG. 13 that the base body 12 of the cassette is welded to the cover foil 14 at the outer edge 64.

The cassette 10 has a recessed centering fork 66 as a positioning aid which receives a centering pin on the machine side on insertion. Stop noses 68 are furthermore molded on which contact against corresponding machine surfaces on insertion. The cassette 10 is thereby guided in height and angle. When pressing the cassette 10 into the fluid treatment machine 100, a latching with the fluid treatment machine takes place at a snap element not shown in more detail here such that the cassette 10 is fixed in an aligned manner. The cassette has a molded handle 70 at the side disposed opposite the centering fork 66 for simplified handling.

The arterial injection septum 16 or the venous injection septum 20 are made in the embodiment shown here, in contrast to a conventional injection position, such that their base body is formed by the base body 12 of the cassette itself so that here only the elastic septum is fixed by a snap ring (not shown in detail here). The septum consists of an elastomer in the embodiment shown here.

Figure 4:
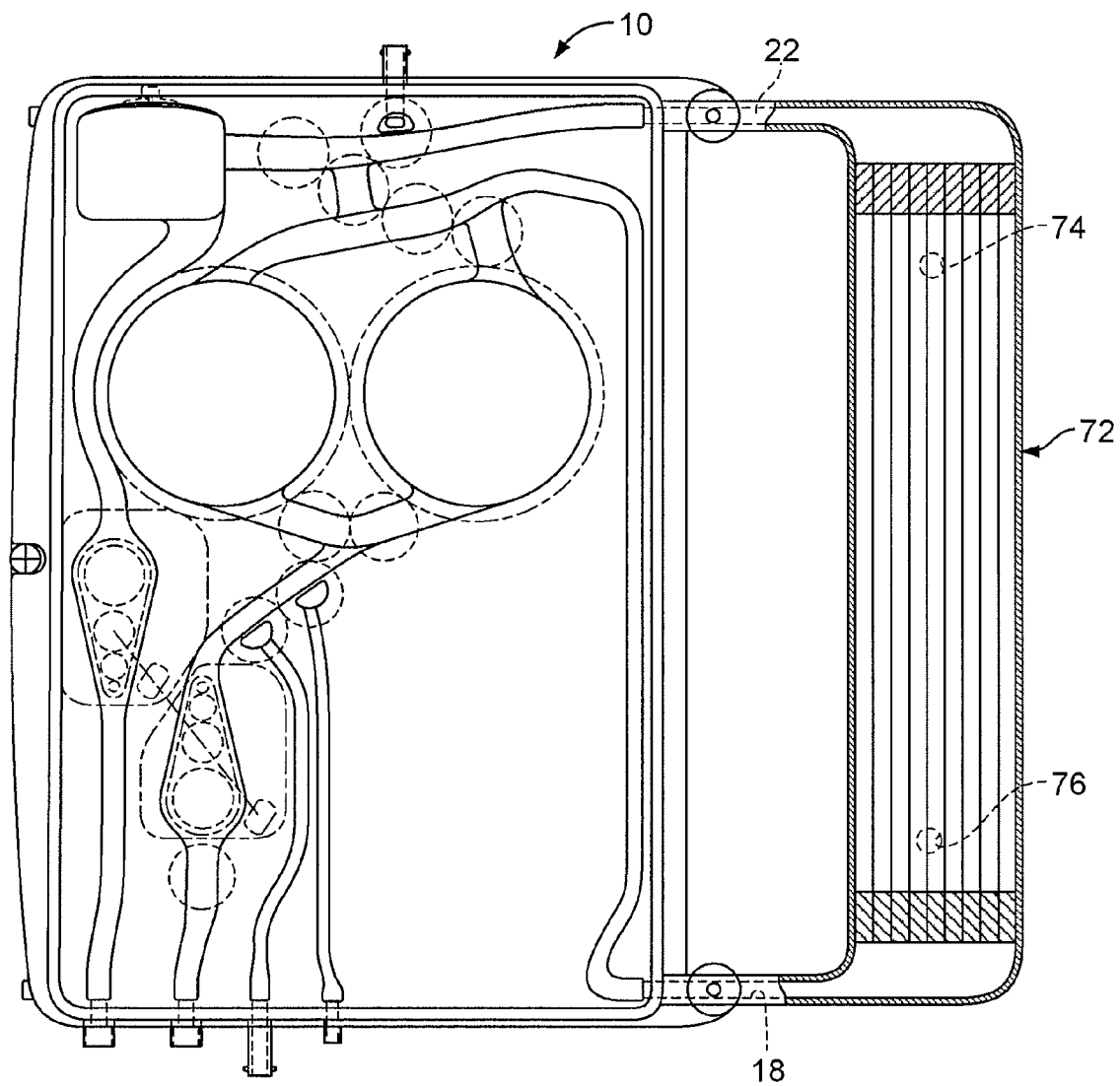
FIG. 4: a schematic plan view of a further aspect of the invention which substantially corresponds to that in accordance with FIG. 1, but has an integrated dialyzer.

FIG. 4 shows a modified embodiment of the cassette in accordance with FIG. 1. This cassette 10 shown in FIG. 4 also serves standard hemodialysis and largely shows an identical design to the cassette 10 in accordance with FIG. 1. To this extent, a detailed description of the already described components of the cassette 10 is superfluous. However, instead of the handle 70 in the embodiment in accordance with FIG. 1, a dialyzer 72 is integrated in the side of the cassette 10, with the lines 18 and 22 to the dialyzer opening directly into the dialyzer. The dialysate connections at the dialyzer, which can have a conventional design, are designated by 74 and 76.

Figure 2:
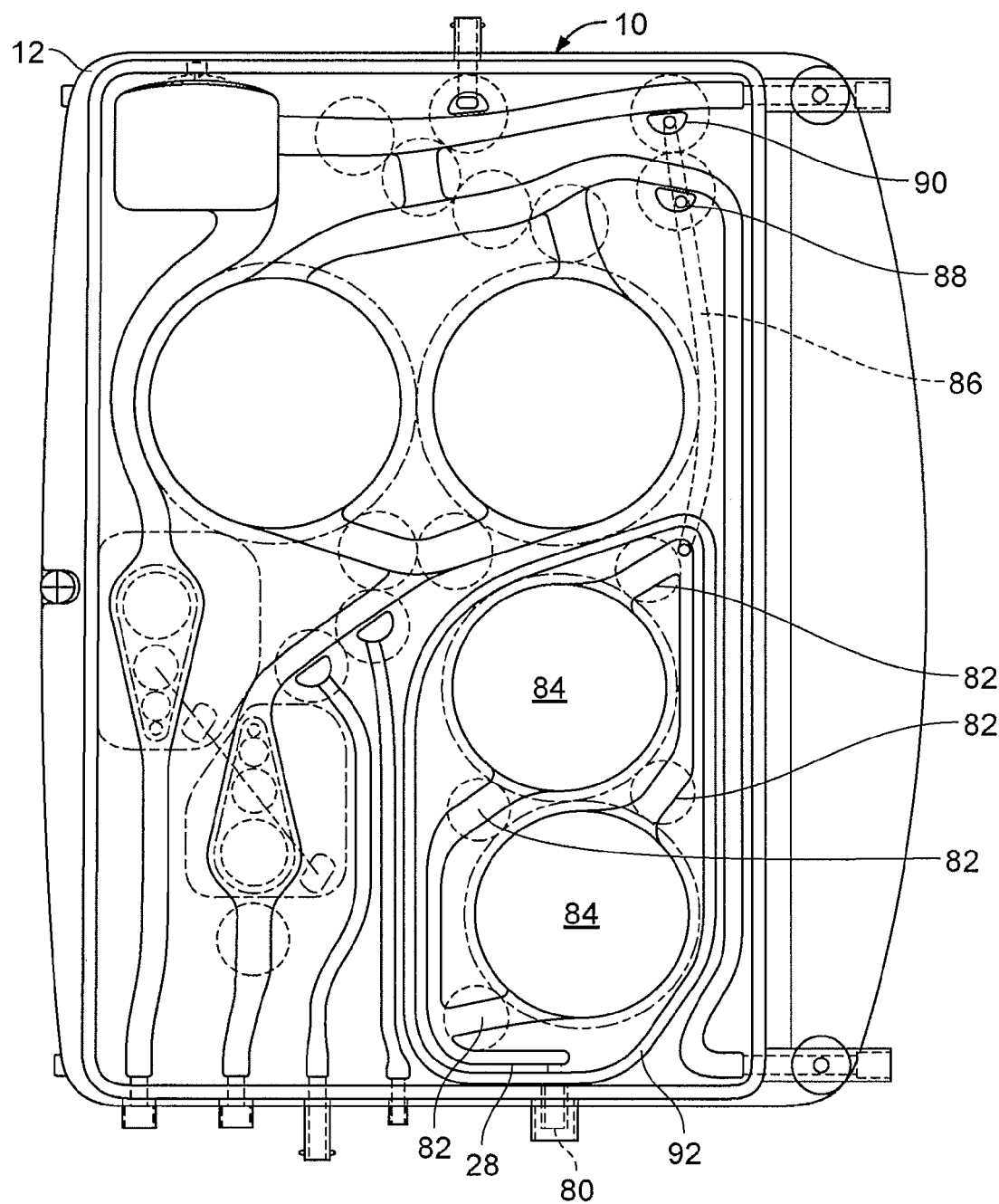
FIG. 2: a schematic plan view of a cassette in accordance with the invention according to a further embodiment of the invention for use in online hemodiafiltration or online hemofiltration.

A cassette 10 is shown in FIG. 2 which is designed as an online hemodiafiltration cassette. It becomes clear from the arrangement of the different elements that the base body 12 of the cassette starts from that base body of a cassette such as has already been described in FIG. 1 with reference to the embodiment for standard hemodialysis. All elements which are known from this configuration can be found in the same manner in the embodiment variant in accordance with FIG. 2 for online hemodiafiltration. To this extent, they will not be additionally explained again. However, those parts will be explained which are necessary for the operation of the hemodiafiltration cassette. This includes the substituate connector 80 via which the substituate fluid is fed into the passages 28. Substituate passage valves 82 are provided at the passages and the passages 28 can be closed at the appropriate positions via these. The substituate fluid is guided into two parallel pump chambers 84, which form substitutate pump chambers, via the passages. The substituate pump chambers 84 substantially correspond to the pump chambers for the blood 50 as they have previously already been described in detail. Starting from the passage 28, the substituate fluid is guided through a substituate tunnel 86 which is disposed on the opposite side of the base body 12 of the cassette. The substituate tunnel is suitably closed at the rear side, e.g. by a welded foil. The substituate fluid 86 can be led into the passage 28 carrying the blood via a port for pre-dilution 88 or via a port for post-dilution 90. The ports are again made as phantom valves here, with reference also again being made here to the construction design in accordance with the German patent application DE 100 53 441.

The substituate region substantially formed by the substituate pump chambers 84 is surrounded by a substituate weld rim 92 to which the cover foil 14 is sealingly welded so that this region of the cassette 10 processing substituate is separated from the blood-carrying region.

Figure 5:
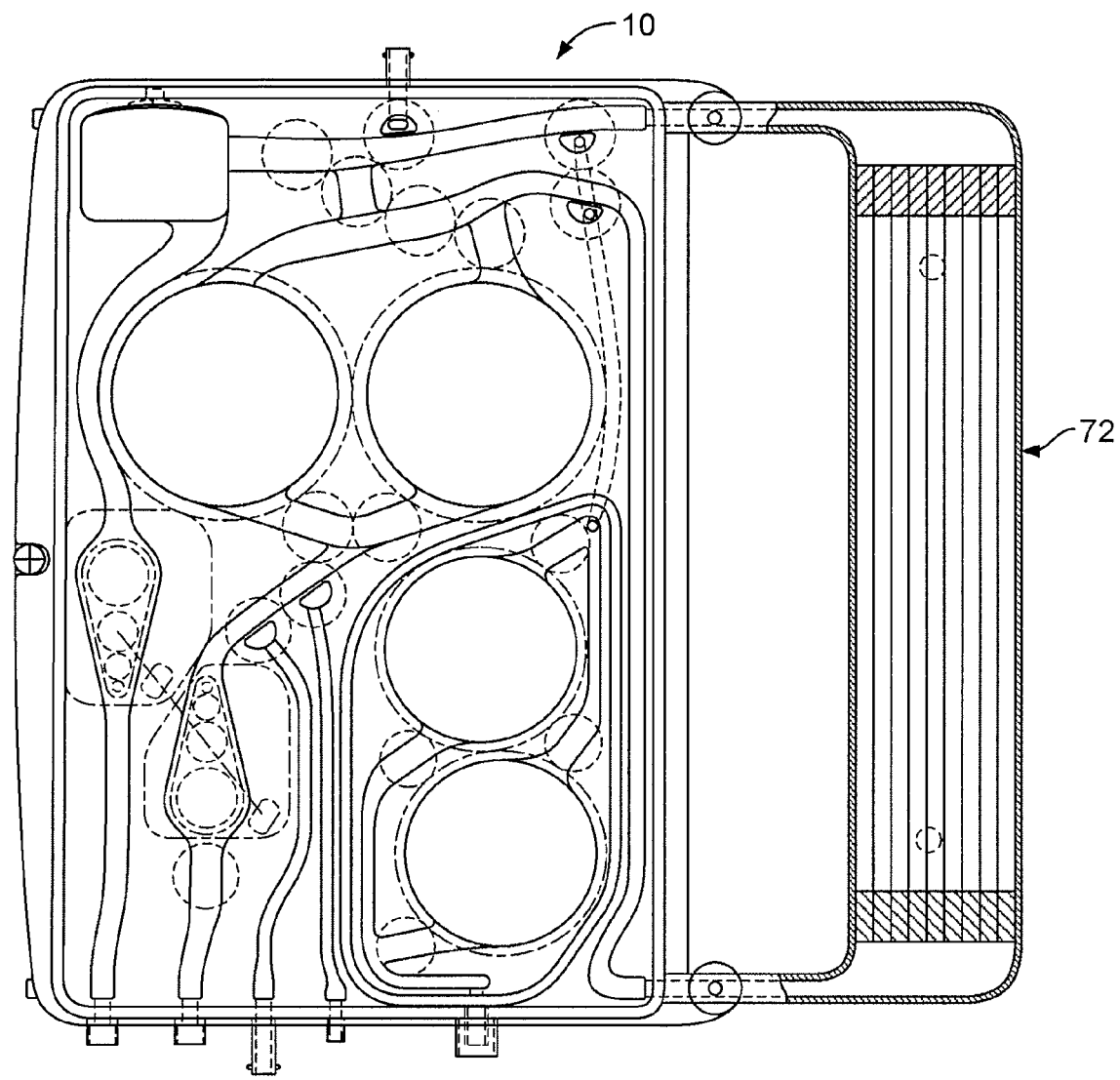
FIG. 5: a further aspect of the invention which substantially corresponds to that in accordance with FIG. 2, but has an integrated dialyzer.

In FIG. 5, a modification of the embodiment variant in accordance with FIG. 2 is shown. Here, too, in a similar manner to the embodiment variant in accordance with FIG. 4, a dialyzer 72 is integrated directly into the cassette 10.

Figure 3:
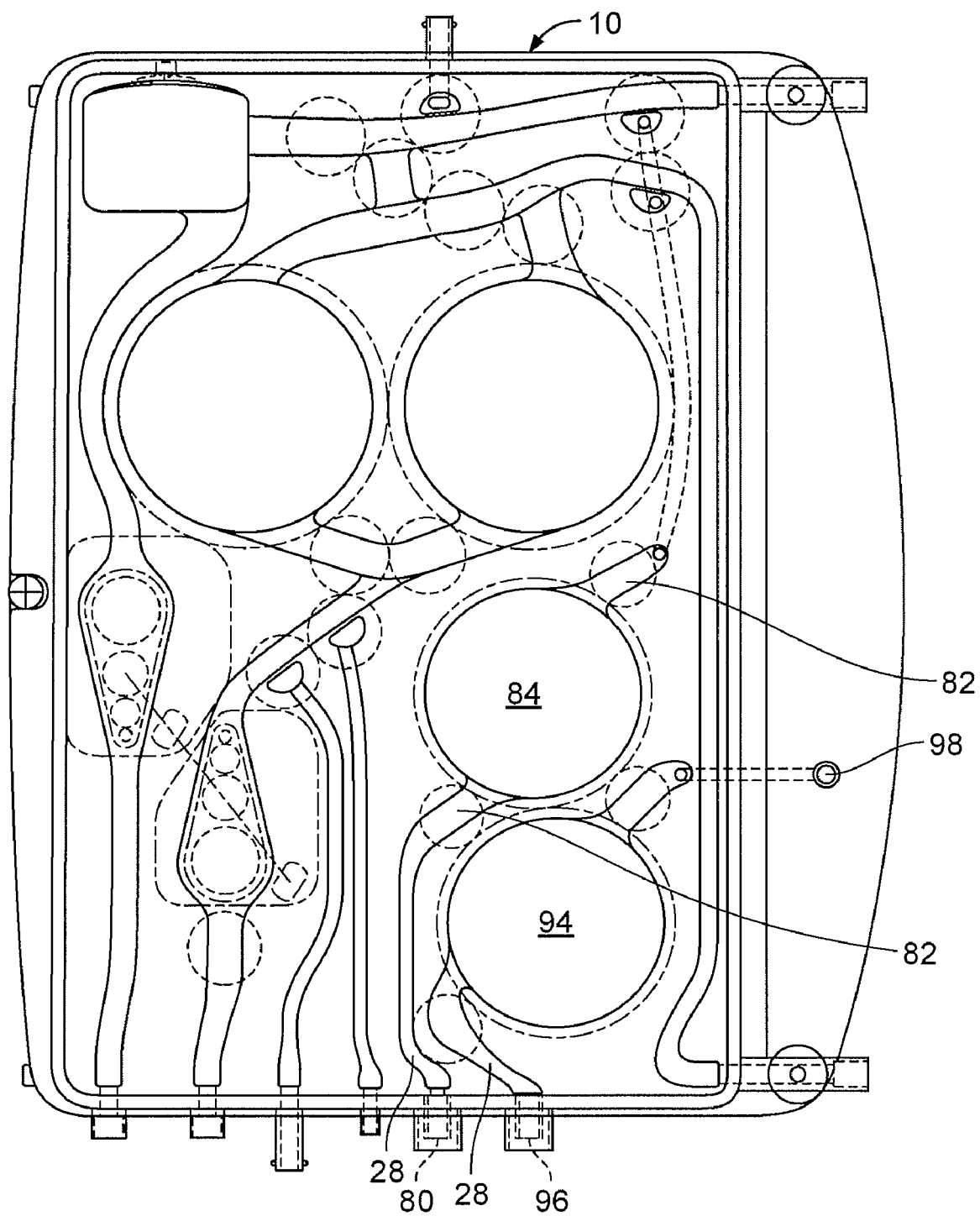
FIG. 3: a plan view of a cassette in accordance with a further embodiment of the present invention which can be used for acute treatment.

In FIG. 3, a cassette 10 for acute treatment is shown as a further integrated embodiment of the cassette. It is designed identically to the embodiment variant in accordance with FIG. 1 in the region of the blood treatment part. With respect to the substituate part, it partly corresponds to the embodiment in accordance with FIG. 2, with here only one substituate pump chamber 84 being provided which is fed by the substituate fluid led in via the substituate connector 80 and the passage 28. In a similar manner as to the embodiment variant in accordance with FIG. 2, substituate passage valves 82 are provided before and after the substituate pump chamber 84. The further pump chamber, which is designated by 94 in the present embodiment variant for acute treatment, is connected to a filtrate outlet 96 via a passage 28 and opens into a filtrate connection 98 which is connected to the dialyzer not shown in any more detail here.

Figure 6:
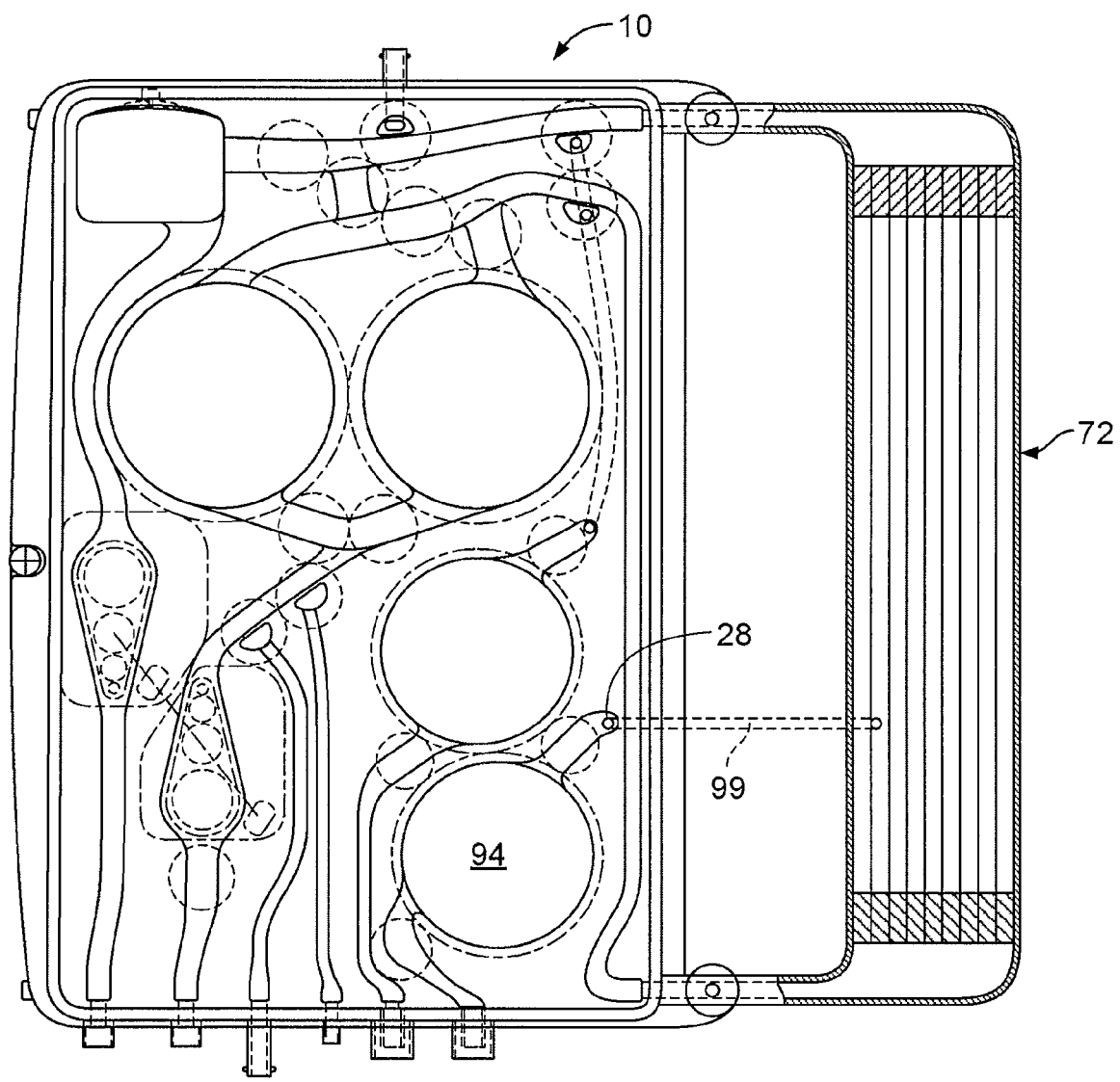
FIG. 6: a further embodiment of the invention which substantially corresponds to that in accordance with FIG. 3, but has an integrated dialyzer.

In FIG. 6, in turn, a modified embodiment variant of the cassette 10 in accordance with FIG. 3 is shown. Here, a dialyzer 72 is in turn integrated instead of the handle, with here a connection 99 being provided between the dialyzer 72 and the passage 28 which carries the filtrate and which leads to the filtrate pump chamber 94.

Figure 7:
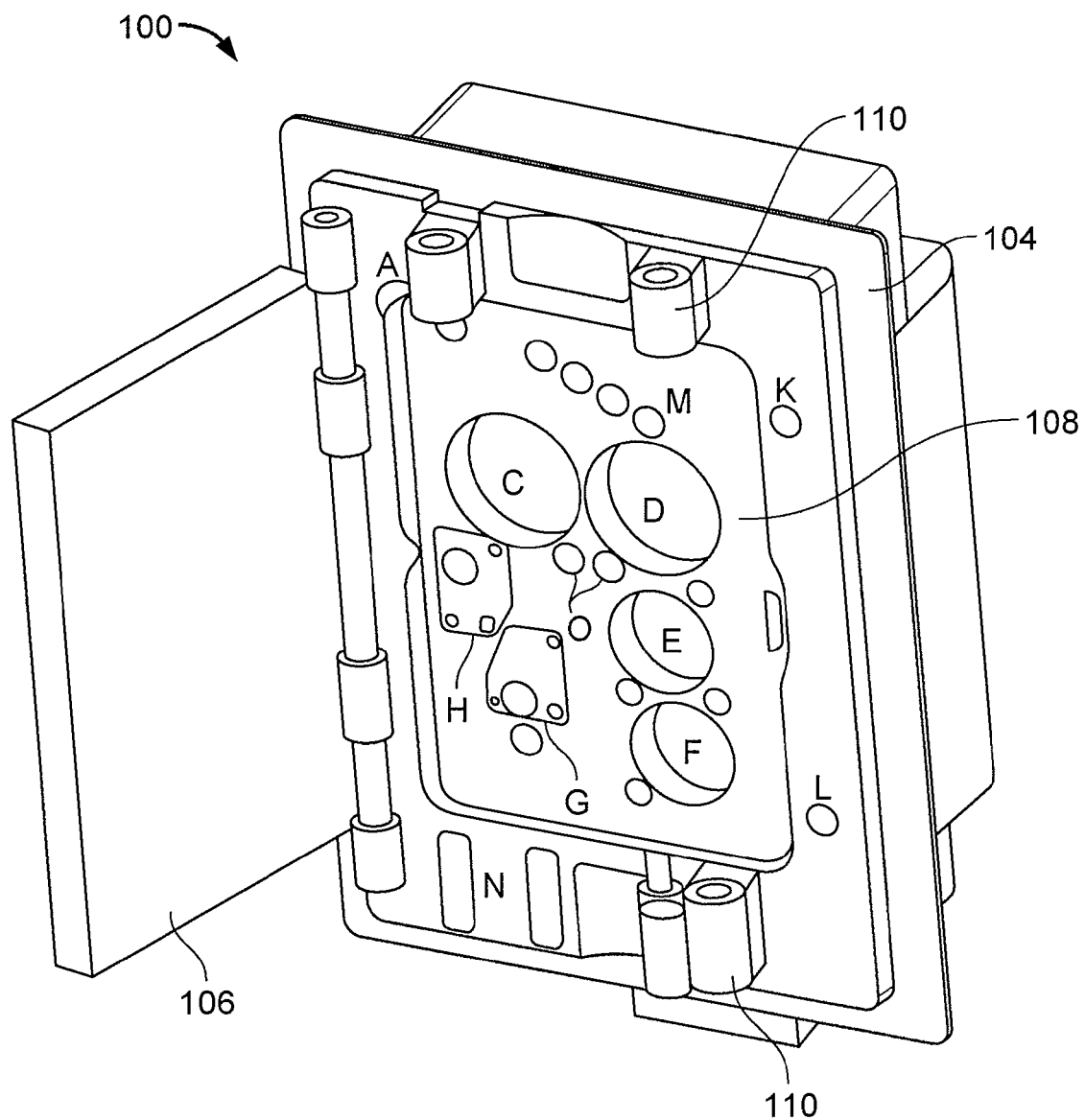
FIG. 7: a three-dimensional representation of a fluid treatment machine as an embodiment of the apparatus in accordance with the invention without an inserted cassette.

In FIG. 7, an embodiment of the fluid treatment machine 100 is shown without an inserted cassette 10. This fluid treatment machine 100 is designed such that all aforesaid cassettes can be inserted, with a basic extracorporeal blood circuit, i.e. a standard dialysis using an external dialyzer, being carried out by a corresponding program selection, for example on insertion of the cassette in accordance with the embodiment variant in accordance with FIG. 1. When a cassette 10 in accordance with the embodiment of FIG. 2 is used, online hemodiafiltration or an online hemofiltration variant is, for example realized by use of the components required for this purpose with, optionally, automatic connections (not shown) to the fluid circuit of the basic unit. Highly integrated variants with an integrated dialyzer and an automatic dialyzer connection are also possible such as are shown by way of the cassette in the embodiment variants in accordance with FIGS. 4 and 5. Acute dialysis treatment is possible when a cassette 10 is used in accordance with the embodiment of FIG. 3.

The fluid treatment machine 100 substantially consists of a frame 104 which surrounds and/or includes or receives the most important components. A door 106 is fitted to the frame 104, on the one hand, and the machine block 108 is guided in the frame, on the other hand. All forces occurring between the door 106 and the interior of the unit are absorbed by means of the frame 104, namely the door hinge, door latch, pressing actuator system and the rear wall. The frame furthermore contains the door latch 110. The cassette 10 is received between the door 106 and the machine block 108, as shown in the FIGS. 8 and 9, and is sealed by pressing. Sensor system elements are included in the cassette region of the machine and they detect whether a cassette is correctly positioned in the fluid treatment machine. These, or further sensor system elements, can be designed such that they are suitable for recognizing the cassette type (e.g. with the aid of a barcode on the cassette).

The important elements for the control and monitoring of the extracorporeal blood circuit such as pumps, valves and the sensor system, etc. are contained in the machine block 108. This machine block 108 establishes the most important interface to the cassette 10. The cassette surface is coupled to the unit here and the sealing of the cassette 10, and thus the fixing of the flow paths, takes place by this. The machine block is guided movably in the frame and fixes the cassette 10, as already described above, until the door is closed.

Figure 8:
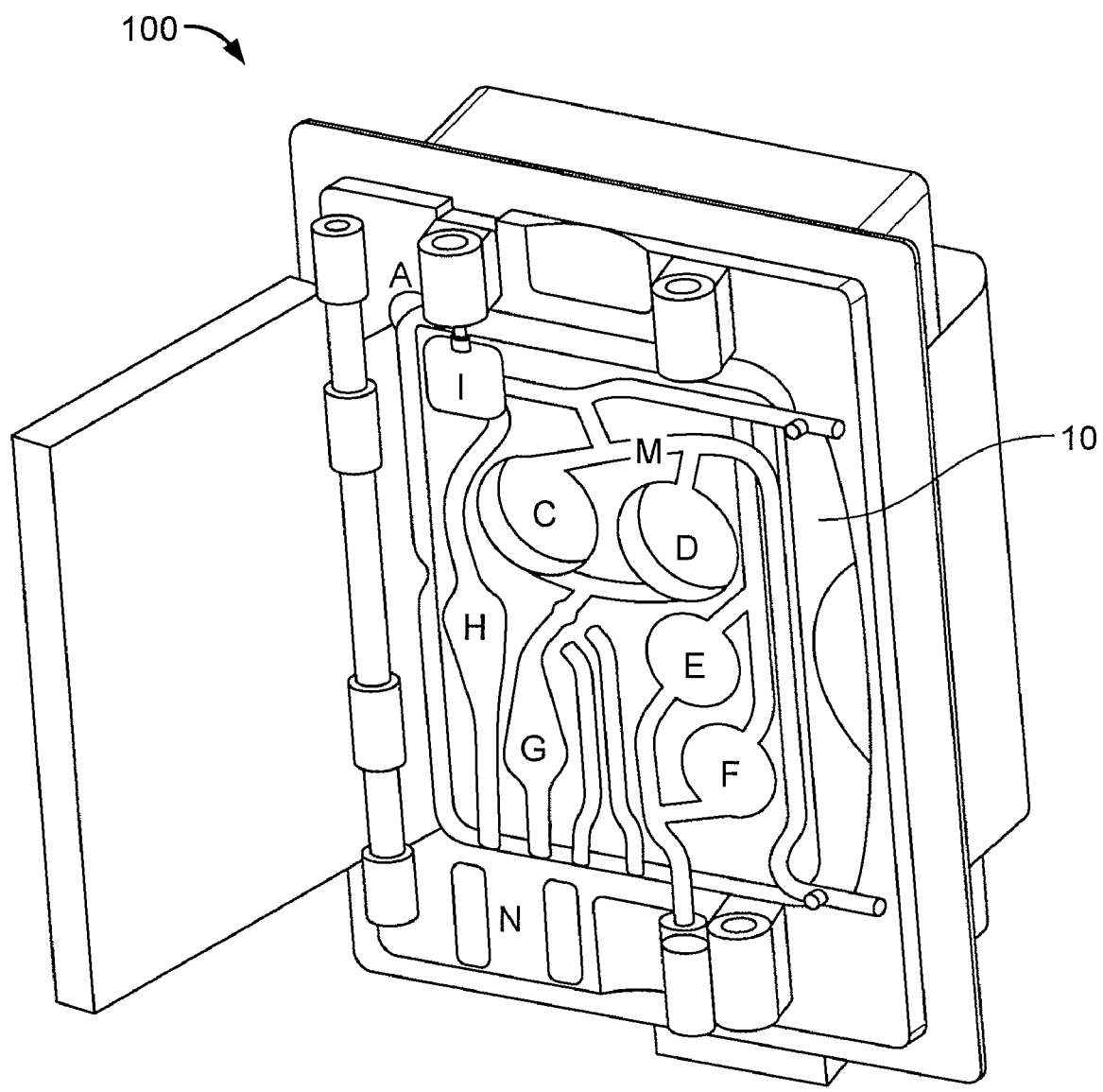
FIG. 8: a representation corresponding to FIG. 7, but with an inserted cassette.
Figure 9:
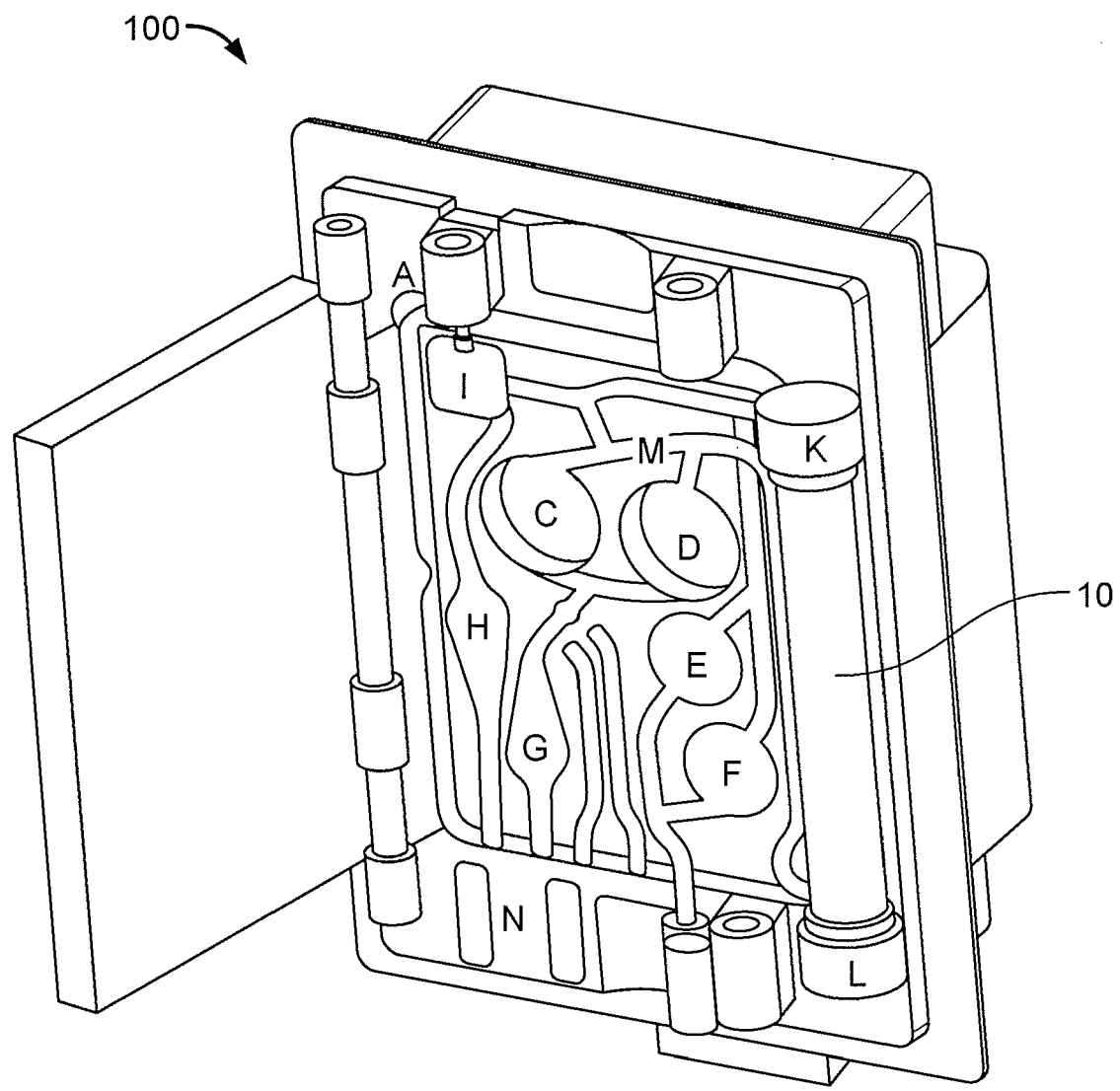
FIG. 9: a representation in accordance with FIG. 7, but with a different embodiment variant of a cassette differing from the cassette shown in FIG. 8.

Hydraulic piston pumps are contained in the fluid treatment machine which are not shown in detail in FIGS. 7, 8 and 9 here. They are, on the one hand, blood pumps or optional substituate feed pumps or ultrafiltrate pumps. They are hydraulically connected to the pump chambers C, D, i.e. to the blood pump chambers, or E, F, i.e. optionally to the optional filtrate pump chambers and/or the optional substituate pump chambers. Furthermore, compressors for the generation of the required pneumatic pressure (overpressure or vacuum) not shown in more detail here are contained in the fluid treatment machine 100. The fluid treatment machine 100 furthermore has—in a manner not shown in more detail—a pneumatic buffer container for the compensation of pressure fluctuations, a main electronics box, a heparin injection pump and a blood pressure monitor module.

A pressing actuator system on the rear wall of the frame 104, likewise not shown in more detail, must be emphasized here. An inflatable air cushion is integrated here which can move the whole machine block 108, which is movably supported in the frame 104, and press it against the closed door 106.

Furthermore, instead of individual air-carrying tubes, an air distributor plate is provided at the machine block 108 which contains main connections for the pneumatics and which guides compressed air and vacuum to the valves and actuators via passages integrated there without any substantial tubing, with them simultaneously terminating the machine block with respect to the interior of the fluid treatment machine 100.

Optional modules can be provided in the fluid treatment machine 100 for the carrying out of the online hemodiafiltration. For instance, an online feed port for the automatic coupling of a cassette 10 to a the dialysate circuit or an online flushing port for the return of flushing solution can be contained here.

The door 106 must be open for the insertion of the cassette 10. The cassette 10 is inserted and, after positioning of the centering fork, is fixed to the cassette on the surface of the machine block by means of a snap hook.

The side of the machine block facing the cassette is lined with a soft elastomer mat not shown in more detail here which seals the cassette 10 after pressing has taken place. A closer description of this elastomer mat has already been given in the German patent application 101 57 924 of the same applicant and reference is made to its full content here.

After closing and locking the door, pressing takes place by inflating the aforesaid air cushion. On opening and removing the cassette, the pressing is cancelled again by letting out the air in the air cushion before opening the door.

To achieve a sufficient pressing and to prevent a tilting of the machine block by a non-uniform introduction of force, the air cushion has approximately the size of the machine block or of the cassette 10.

Since, however, further components, for example, control valves or the air distributor plate with the control valves, are now disposed between the air cushion and the machine block, the force transmission takes place by means of spacer bolts.

The traction between the door 106, the frame 104 and the rear wall takes place by the door hinge, the latch 110 and connection bolts, not shown in any more detail here, between the frame and the rear wall.

As already mentioned, a constant pressing of the cassette 10 must take place for a proper operation. For this purpose, it is necessary for the door to be locked during the treatment. This locking takes place via two latching bolts (not shown in any more detail here) at the upper right hand and lower right hand door region, with these moving into two corresponding bores inside the door 106 on actuation, which takes place automatically. The moving in and out takes place pneumatically. An erroneous opening of the door on a failure of the pneumatics is precluded by the bolts moved into the door and by the lateral forces occurring by the pressure load of the door. To check whether the latching has taken place, Hall proximity sensors can be integrated which detect the movement of the bolts. In addition, this signal can be linked to information on the door position which can be picked up by a separate sensor. In addition, the latching bolt not shown in any more detail here can have a latch connection. This latch connection consists of a spring-loaded latch ball on the door side which latches into a corresponding arch of the latch bolt and can hold the door in the corresponding position. An introduction slope is provided for the simplified latching. To open the door from the latch position, the latch ball present here is drawn back by means of a mechanical system.

On the side of the fluid treatment machine 100, the blood circuit substantially consists of at least one hydraulically controlled membrane pump having two independent pump chambers C and D which can be used as a highly precise flow pump or as a volumetric metering unit, a row of valves M, O and clamps N for the control of the flow path, a highly integrated sensor system G, H required for monitoring and control, an active air extractor, i.e. an air separation chamber I with a connected cassette venting A, of the blood circuit (air-free circuit) and a door 106 to fix the cassette.

The fluid treatment machine 100 respectively comprises a pneumatic system for the overpressure and a pneumatic system for the underpressure. The underpressure serves, for example, to apply an underpressure between the foil 14 of the cassette 10 and the unit side to prevent a passage restriction on the plastic deformation of the foil, to raise the foil at feed positions and thus to be able to keep the access free, to avoid air compliance in the pump devices and to be able to ensure an air-free coupling between the sensor and the foil at specific sensor positions. The air suction requires openings in the unit side and a suction unit, i.e. a vacuum pump, connected to it, wherein the vacuum distribution should be ensured as uniformly and as reliably as possible over the whole surface. In the idling state, the openings should be at least largely closed to permit a good cleaning here. In operation, however, a problem-free air suction should be possible. This problem is solved by the aforementioned elastomer mat which was described in the German patent application 101 57 924.

In the cassette 10, no passage seals are contained except for the edge region and some safety weld connections. The sealing of all flow paths and passages must therefore take place by pressing. For this purpose, the cassette has sealing beads 52 on the passage rims which have already been described above and which are sealable on the pressing of the disposables between the machine block 108 and the door 106 by pressing into the elastic mat.

The air distributor plate not shown in any more detail here is located on the rear side of the machine block 108 and is connected to the, for example, two membrane pumps of the pneumatic system, namely the overpressure pump and the underpressure pump. The air distributor plate is sealed with respect to the rear side of the machine block by a sealing mat and permits the compressed air and vacuum feed via integrated passage structures so that every valve does not need its own tubing. A plurality of circuits are present on the air distributor plate, namely a vacuum circuit, a compressed air circuit which is directly connected to the compressor for the supply of components which always need compressed air, a compressed air circuit for the protection of sensitive components which may only be charged with compressed air under certain states, with it also being separable from the compressor by an on/off valve and an exhaust circuit.

By integration of a plurality of control valves on the air distributor plate, the electrical supply can also be collected via a small control board. Since a plurality of valves are only needed with specific options, a modular retrofitting capability must be ensured.

The sensor system and the pump connections are guided through the plate through apertures and cut-outs.

Sensors which are collected in integrated sensor modules in the present fluid treatment machine 100 are required for the monitoring and control of the extracorporeal blood circuit. Two respective modules work together as a pair. One module is accommodated in the door 106 and the counter-piece in the machine block 108. Both the arterial branch should be monitored by the arterial measuring chamber G and the venous branch by the venous measuring chamber H. The integrated measurement sensor system is described in detail in the German patent applications DE 198 37 667 A and DE 101 43 137 of the same patent applicant. The sensors together have i.a. the following properties or provide the following possibilities:

measurement and monitoring of the blood volume;
measurement of the hematocrit;
measurement and monitoring of the thermal energy balance;
measurement and monitoring of the body temperature;
measurement of the conditions of the fistula (with circulation);
air detection;
fistula pressure measurement.

A multi-sensor module is usually fitted with an ultrasonic sensor for volume monitoring, measurement of the hematocrit and the air detection, with a temperature sensor for the automatic access analysis, body temperature monitoring and thermal energy balance, with a pressure sensor for the pressure monitoring and with an optical sensor for the automatic detection of blood.

Reference is again made to DE 100 46 651 A1 with respect to the valves M and the pump valves O with regard to their design.

In addition to the aforesaid valves which are shown in FIG. 7, so-called phantom valves, which are not drawn in any more detail in this FIG. 7, are additionally present. Reference can be made to DE 100 53 441 A1 with respect to the design and the function of the phantom valves.

N designates safety clamps which serve to achieve a safe state during an alarm in the extracorporeal blood circuit, with them interrupting the patient line and thus any blood flow from or to the patient. To avoid unwanted compliance effects, and since the system is designed for a flow reversal, this safety function must be ensured both on the arterial side and on the venous side so that two blocking clamps N are used which can be mechanically coupled.

The blocking clamps should be effective as close to the patient as possible in order to be able to minimize any interference and to satisfy high safety demands. For this reason, tube clamps are used which act directly on the patient tubes.

A possible embodiment, such as is provided here, consists of the clamping of the tubes against a clamping rail on the inner side of the door by means of a reclosable pneumatically opened clamping slide. Such a system is passively spring-closing, namely without pressure and without current and so is also advantageous in the case of a failure under safety aspects.

In FIG. 8, a fluid treatment machine 100 is shown corresponding to FIG. 7 with an inserted cassette 10 corresponding to FIG. 2. In FIG. 9, in contrast, a fluid treatment machine 100 is shown with a cassette 10 corresponding to the embodiment variant in accordance with FIG. 5, with the dialyzer in the cassette here having an automatic dialysate connection K and L to the fluid treatment machine 100.

The new apparatus shown here follows a strictly modular approach while achieving a high flexibility and deployment possibility also with respect to future deployment possibilities and options. The integrated blood module permits the carrying out of the whole spectrum of the blood treatment procedures, namely standard hemodialysis, online hemodiafiltration, online hemofiltration and also acute treatment.

It must be pointed out with respect to the acute treatment that the machines serving the acute treatment, i.e. the acute dialysis or acute filtration, have to have a simple design in order to be able to be transported correspondingly easily and to be able to work without a complex supply structure (e.g. water connection). In this system, therefore, work is carried out practically without exception with bags with premanufactured solutions. Using the embodiments shown in FIGS. 3 to 6, acute hemofiltration can then be carried out easily in which the substituate is supplied from a bag and filtrate is removed from the filter into an empty bag with the pumps shown. Except for the connection of the bags, no further measure is necessary in this case. It would naturally nevertheless be possible to additionally make a dialysis possible with a corresponding effort. Furthermore, the substituate pump could alternatively be used as a dialysate supply pump if the connections inside the cassette were changed accordingly. Then dialysis fluid filled into bags could be supplied in balanced form to the filter via the membrane pump, while fluid is led out in a controlled manner via the filtrate pump. No further components would also be necessary for the fluid control in such a machine.

Each of these types of treatment can take place both in two-needle and in single-needle mode. Reference is made here to the German patent DE 100 42 324 C1 with respect to the description of the two-needle or single-needle mode.

A series of new developments is included in the invention shown here such as the innovative design of the pump chamber and the associated spherical pump surface at the machine side and also the air separation chamber. Protection is claimed for these components or cassettes or machines for blood treatment in isolation within the framework of the invention, this is without interaction with other elements of the cassettes or machines.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An apparatus for the treatment of a medical liquid, the apparatus comprising:

a liquid treatment machine having a compartment configured to contain either one of first and second cassettes, the first cassette having a rigid base body with a first chamber and passages, and a foil that covers the first chamber and passages, the second cassette having a rigid base body with first and second chambers and passages, and a foil that covers the first and second chambers and passages, the first chamber of the first cassette positioned to correspond to the first chamber of the second cassette, and the second chamber of the second cassette positioned to correspond to a region of the first cassette that does not include a chamber, the liquid treatment machine having a machine block and including first and second actuators, the first actuator being aligned with the first chamber of the first cassette when the first cassette is disposed in the compartment of the liquid treatment machine, the first actuator being aligned with the first chamber of the second cassette when the second cassette is disposed in the compartment of the liquid treatment machine, the second actuator being aligned with the region of the first cassette that does not include a chamber when the first cassette is disposed in the compartment of the liquid treatment machine, and the second actuator being aligned with the second chamber of the second cassette when the second cassette is disposed in the compartment of the liquid treatment machine, wherein the liquid treatment machine is adapted so that the first actuator and not the second actuator is operated when the first cassette is disposed in the compartment of the liquid treatment machine and both the first and second actuators are operated when the second cassette is disposed in the compartment of the liquid treatment machine.

2. The apparatus in accordance with claim 1, wherein the cassettes are disposable.

3. The apparatus in accordance with claim 1, wherein the first cassette can be used for a first type of treatment, and the second cassette can be used for a second type of treatment, the first type of treatment being different than the second type of treatment.

4. The apparatus in accordance with claim 3, wherein the liquid treatment machine is adapted to perform any one of standard hemodialysis, online hemodiafiltration, online hemofiltration, and acute treatment.

5. The apparatus in accordance with claim 1, wherein each cassette has a molded handle at a side of the rigid base body of the cassette.

6. The apparatus in accordance with claim 5, wherein a dialyzer is integrated at the side of the base body of each cassette, the dialyzer forming the handle.

7. The apparatus in accordance with claim 1, wherein the liquid treatment machine has a frame to which a door is fitted and in which the machine block is guided, with the door and the machine block being alignable with respect to one another such that either of the cassettes can be received between the door and the machine block in a sealed manner.

8. The apparatus in accordance with claim 7, further comprising a pressing actuator system that provides an air cushion to move the machine block toward the closed door for the sealing reception of one of the cassettes.

9. The apparatus in accordance with claim 7, wherein the machine block includes valves, and further comprising an air distributor plate with integrated passages that adjoins the machine block and that is configured to conduct compressed air and/or a vacuum from corresponding pneumatic connections to the actuators and the valves in the machine block.

10. The apparatus in accordance with claim 1, wherein the liquid treatment machine includes at least one projection arranged to fit into a centering recess defined in at least one of the cassettes when the at least one of the cassettes is disposed in the compartment of the liquid treatment machine, and the liquid treatment machine includes at least one stop arranged to fix the at least one of the cassettes on a surface of the machine block when the at least one of the cassettes is disposed in the compartment of the liquid treatment machine.

11. The apparatus according to claim 10, wherein the stop is a snap-in hook.

12. The apparatus in accordance with claim 1, wherein a door can be latched to a frame after the door is closed, with the latched state being monitorable via sensors.

13. The apparatus in accordance with claim 1, wherein an elastic mat is arranged between one of the cassettes and the machine block when the one of the cassettes is disposed in the compartment of the liquid treatment machine.

14. The apparatus in accordance with claim 13, wherein the elastic mat has recesses for a pump chamber to be provided and mat passages which extend along liquid-carrying passages of one of the cassettes when the one of the cassettes is disposed in the compartment of the liquid treatment machine.

15. The apparatus in accordance with claim 1, wherein sensor modules are integrated in the liquid treatment machine for the determination of the parameters of the medical liquid to be treated and which are each designed in pairs and of which one part of the pair is installed in the machine block and the other part in a door.

16. The apparatus in accordance with claim 1, wherein a venting unit is integrated in the liquid treatment machine which can be coupled to a gas-permeable membrane integrated in one of the cassettes when the one of the cassettes is disposed in the compartment of the liquid treatment machine.

17. The apparatus in accordance with claim 1, wherein the liquid treatment machine comprises a sensor adapted to distinguish the first cassette from the second cassette when the cassettes are disposed in the compartment of the liquid treatment machine.

18. The apparatus in accordance with claim 17, wherein the sensor comprises a barcode reader arranged to read a barcode on the first cassette when the first cassette is disposed in the compartment of the liquid treatment machine and arranged to read a barcode on the second cassette when the second cassette is disposed in the compartment of the liquid treatment machine.

19. The apparatus in accordance with claim 1, wherein at least one of the actuators is a pump.

20. The apparatus in accordance with claim 1, wherein at least one of the actuators is a valve.

21. The apparatus in accordance with claim 1, wherein the liquid treatment machine and the first cassette are adapted to perform standard hemodialysis when the first cassette is disposed in the compartment of the liquid treatment machine.

22. The apparatus in accordance with claim 1, wherein the liquid treatment machine and the second cassette are adapted to perform online hemodiafiltration when the second cassette is disposed in the compartment of the liquid treatment machine.

23. A system for the treatment of a medical liquid, the system comprising:
   first and second cassettes, the first cassette having a rigid base body with a first chamber and passages, and a foil that covers the first chamber and passages, the second cassette having a rigid base body with first and second chambers and passages, and a foil that covers the first and second chambers and passages, the first chamber of the first cassette positioned to correspond to the first chamber of the second cassette, and the second chamber of the second cassette positioned to correspond to a region of the first cassette that does not include a chamber; and
   a liquid treatment machine having a compartment configured to contain either one of the first and second cassettes, the liquid treatment machine comprising first and second actuators, the first actuator being aligned with the first chamber of the first cassette when the first cassette is disposed in the compartment of the liquid treatment machine, the first actuator being aligned with the first chamber of the second cassette when the second cassette is disposed in the compartment of the liquid treatment machine, the second actuator being aligned with the region of the first cassette that does not include a chamber when the first cassette is disposed in the compartment of the liquid treatment machine, and the second actuator being aligned with the second chamber of the second cassette when the second cassette is disposed in the compartment of the liquid treatment machine,
   wherein the liquid treatment machine is adapted so that the first actuator and not the second actuator is operated when the first cassette is disposed in the compartment of the liquid treatment machine and both the first and second actuators are operated when the second cassette is disposed in the compartment of the liquid treatment machine.

24. The system in accordance with claim 23, wherein the base body of each cassette is formed of polypropylene.

25. The system in accordance with claim 23, wherein the cover foil of each cassette is formed of a polyolefin elastomer mixture.

26. The system in accordance with claim 23, wherein a venting chamber is formed by a molding in the base body of each cassette and by the cover foil of each cassette, and the cover foil can be sucked into a recess formed in the liquid treatment machine.

27. The system in accordance with claim 23, wherein the first chamber of each cassette is a pump chamber, and the actuator of the liquid treatment machine that aligns with the first chamber is a pump.

28. The system in accordance with claim 27, wherein the pump chamber has an inlet and an outlet that are substantially tangential to each other.

29. The system in accordance with claim 28, wherein the pump chamber has a shape of a spherical section and wherein a standing bead is formed such that a flushing passage is formed between an upper edge of the base body of the cassette and the cover foil in a pressing-out phase.

30. The system in accordance with claim 29, wherein a spherical surface of the pump has a smaller radius than the pump chamber such that a flushing passage is formed between the spherical surface of the pump and the pump chamber when the pump is inserted into the pump chamber.

31. The system in accordance with claim 23, wherein each of the cassettes further comprises at least one measuring chamber that has a shape of a diffuser nozzle.

32. The system in accordance with claim 23, wherein wherein the base body of each cassette comprises an edge bead along all passages and chambers, and the edge bead faces the cover foil.

33. The system in accordance with claim 23, wherein the base body of each cassette is welded to the cover foil at an outer edge and wherein a substitute-carrying region in the cassette is surrounded by a weld seam.

34. The system in accordance with claim 23, wherein each cassette is operable in a two-needle or a single-needle operation.

35. The system in accordance with claim 23, wherein the liquid treatment machine and the first cassette are adapted to perform standard hemodialysis when the first cassette is disposed in the compartment of the liquid treatment machine.

36. The system in accordance with claim 23, wherein the liquid treatment machine and the second cassette are adapted to perform online hemodiafiltration when the second cassette is disposed in the compartment of the liquid treatment machine.

37. The system in accordance with claim 23, wherein the cassettes are disposable.

38. The system in accordance with claim 23, wherein the first cassette can be used for a first type of treatment, and the second cassette can be used for a second type of treatment, the first type of treatment being different than the second type of treatment.

39. The system in accordance with claim 38, wherein the liquid treatment machine is adapted to perform any one of standard hemodialysis, online hemodiafiltration, online hemofiltration, and acute treatment.

40. The system in accordance with claim 23, wherein at least one of the actuators is a valve.

* * * * *

UNITED STATES PATENT AND TRADEMARK OFFICE
CERTIFICATE OF CORRECTION

PATENT NO. : 7,648,627 B2  Page 1 of 1
APPLICATION NO. : 10/516528
DATED : January 19, 2010
INVENTOR(S) : Josef Beden It is certified that error appears in the above-identified patent and that said Letters Patent is hereby corrected as shown below:

Claim 32, column 14, line 25:
 after "wherein" and delete --wherein--.

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

PATENT NO.      : 7,648,627 B2                         Page 1 of 1
APPLICATION NO. : 10/516528
DATED           : January 19, 2010
INVENTOR(S)     : Beden et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 726 days.

Signed and Sealed this

Twenty-third Day of November, 2010

David J. Kappos
*Director of the United States Patent and Trademark Office*